US006180381B1

(12) United States Patent
Montgomery et al.

(10) Patent No.: US 6,180,381 B1
(45) Date of Patent: Jan. 30, 2001

(54) PSEUDOMONAS CHLORORAPHIS MICROORGANISM, POLYURETHANE DEGRADING ENZYME OBTAINED THEREFROM, AND METHOD OF USE

(75) Inventors: Michael T. Montgomery, Laurel; James R. Campbell, Olney, both of MD (US); Joel R. Crabbe, Temple, TX (US); Steven E. Walz, Annapolis, MD (US); Laura Thompson, Greenville, SC (US)

(73) Assignee: The United States of America as represented by the Secretary of the Navy, Washington, DC (US)

( * ) Notice: Under 35 U.S.C. 154(b), the term of this patent shall be extended for 0 days.

(21) Appl. No.: 09/016,296

(22) Filed: Jan. 30, 1998

Related U.S. Application Data

(62) Division of application No. 08/414,837, filed on Mar. 31, 1995, now Pat. No. 5,714,378.

(51) Int. Cl.[7] ............................... C12N 9/14; C12N 9/16; C12N 1/20
(52) U.S. Cl. .......................... 435/196; 435/183; 435/195; 435/252.3; 435/262.5; 435/252.34
(58) Field of Search ..................................... 435/243, 244, 435/252.3, 252.34, 320.1, 262, 262.5, 280, 196

(56) References Cited

U.S. PATENT DOCUMENTS

| | | |
|---|---|---|
| 2,607,359 | 8/1952 | Oesting . |
| 4,067,773 | 1/1978 | Martin . |
| 4,154,653 | 5/1979 | Hatakeyama et al. . |
| 4,736,866 | 4/1988 | Leder et al. . |
| 5,085,999 | 2/1992 | Bowers-Irons et al. . |
| 5,320,955 | 6/1994 | Meyers et al. . |
| 5,322,686 | 6/1994 | Grahn et al. . |
| 5,328,839 | 7/1994 | Aharonowitz et al. . |
| 5,328,845 | 7/1994 | Finkelstein et al. . |
| 5,336,492 | 8/1994 | Payne et al. . |
| 5,342,778 | 8/1994 | Moriya et al. . |
| 5,344,770 | 9/1994 | Hitomi et al. . |

OTHER PUBLICATIONS

Kay MJ et al. Chemical and Physical changes occuring in polyester polyurethane during biodegradation. Int.Biodet. Biodeg. Mar. 1993, vol. 31:209–225.*

Thompsoon LK et al. Use of transposon–generated mutants fot the study of polyurethane degradation by Pseudomonads. Abstracts of 94th General Meeting of ASM, May 23–27, 1994. Abstract No. Q–462.*

Tascon RI et al. Transposon mutagenesis in *A.pleuropneumoniae* with a Tn10 derivative. J. Bacteriol., Sep. 1993, vol. 175(17):5717–5722.*

Smirnov SP et al. Induction of transposon Tn1 translocation in UV–irradiated *E. coli* cells. Genetika, Mar. 1981, vol. 17(3):420–423.*

Crabbe et al. Biodegradation of a colloidal ester–based polyurethane by soil fungi. Int. Biodet. Biodeg. Mar. 1994, vol. 33:103–113.*

M.J. Day et a., "Bacterial Degradation of Polyester Polyurethane", BIOSIS Entry 91:340367, citing Int. Biodeterior, 27(2) 205–222.

M. Sato, "Deterioration of Polyurethane Filaments With Fungal Enzymes, Aspergillus niger FERM J–1 and Cladosporium cladosporoides FERM J–8", Chem Absts. 95:64, Abst. 99192, citing Sen'i Gakkaishi 37(7), T290–T300.

Mahmoud et al., "Biodegradation and Biostripping of Polyurethan Coatings By Hydrocarbon–Degrading Bacteria", Zag. J. Pharm., vol. 3, No. 2, Aug. 1994, 23–31.

\* cited by examiner

*Primary Examiner*—Rebecca E. Prouty
*Assistant Examiner*—Manjunath Rao
(74) *Attorney, Agent, or Firm*—John J. Karasek; Amy L. Ressing

(57) ABSTRACT

Wild-type bacteria with polyurethanase activity, and the ability to excrete polyurethanase into a culture medium have been genetically altered to significantly increase their polyurethanase activity. Biologically pure cultures of these genetically altered are cultured in a medium containing an inducer for the production of polyurethanase. The bacteria are then removed from the culture medium to provide a preparation with a high polyurethanase activity. One useful genetically altered bacteria is a strain of Pseudomonas chlororaphis designated ATTC No. 55729. The polyurethanase-containing preparation may then be used directly to degrade polyurethane, particularly polyurethane and polyurethane-based coatings.

4 Claims, No Drawings

PSEUDOMONAS CHLORORAPHIS MICROORGANISM, POLYURETHANE DEGRADING ENZYME OBTAINED THEREFROM, AND METHOD OF USE

This is a division of application Ser. No. 08/414,837, filed Mar. 31, 1995, to Montgomery et al., titled "PSEUDOMONAS CHLORORAPHIS MICROORGANISM, POLYURETHANE DEGRADING ENZYME, OBTAINED THEREFROM, AND METHOD OF USE" now U.S. Pat. No. 5,714,378 issued Feb. 3, 1998.

BACKGROUND OF THE INVENTION

1. Field of the Invention

The present invention relates generally to the degradation of polyurethane and more specifically to the enzymatic degradation of polyurethane.

2. Description of the Related Art

Polyurethanes are a diverse group of man-made polymers of considerable economic importance that have a wide range of chemical and physical properties. Polyurethane-based coatings, such as polyurethane paint, are used on many structures such as buildings, vehicles, boats, and aircraft. One of the main benefits of using polyurethane-based coatings is the environmental resistance of polyurethane. However, the environmental resistance also makes it difficult to remove.

Currently, polyurethane-based coatings are removed, for repair and repainting, using organic solvents such as methlyene chloride. However the use of methylene chloride creates large amounts of toxic waste. In fact, some uses of methylene chloride are banned in some States. Alternatively, polyurethane-based coatings are removed using blast cleaning with plastic beads. However, the blasting can damage some types of composite surfaces being cleaned. Moreover, the spent plastic beads create new waste disposal problems. Also, the polyurethane particles removed are not degraded to harmless components.

As an alternative, biological degradation of polyurethane has been proposed. Biological degradation of naturally-occurring polymers, such as chitin and cellulose, involves induction of hydrolytic enzymes by soluble oligomers released form the polymer surface. Through the oligomers, the hydrolytic enzymes break down the polymer into biologically digestible components. However, induction of enzymes for degrading a synthetic polyurethane-coated surface is more difficult because of the lack of soluble material (oligomers) released from weathered, painted surfaces. Accordingly, the direct use of microbes to degrade polyurethane coatings on surfaces is impractical.

SUMMARY OF THE INVENTION

Accordingly, it is an object of this invention to remove a polyurethane coating from a surface without the use of organic solvents or abrasives.

It is a another object of the present invention to remove a polyurethane coating from a surface in an environmental acceptable manner.

It is a further object of the present invention to remove a polyurethane coating from a surface without damaging the surface being cleaned.

These and other objects are achieved by a enzymatic preparation obtained from the culture of a newly developed, man-made mutant strain of *Pseudomonas chlororaphis* that has an enhanced ability to degrade polyurethane. Additionally, a system for the isolation and generation of mutant strains of bacteria having an enhanced ability to degrade polyurethane is disclosed.

DESCRIPTION OF THE PREFERRED EMBODIMENTS

Despite their synthetic polymeric origins, some polyurethanes are susceptible to microbial degradation. Though the specific biological mechanisms are responsible for degradation have not been well-characterized, polyurethanes contain several chemical linkages (bonds) that could be enzymatically hydrolyzed including ester, amide, urethane, urea, and biuret bonds. It has been possible to isolate microorganisms from polyurethane-coated surfaces in the environment.

One microorganism used in the present invention is a mutant strain of *Pseudomonas chlororaphis* designated BC2-12. A subculture of the microorganism may be obtained from the permanent collection of the American Type Culture Collection, 12301 Parklawn Drive, Rockville, MD 20852, where it was deposited on Dec. 14, 1995 and received the number ATCC 55729. The original wild-type microorganism was isolated from a nutrient enrichment culture using weathered paint chips as the inoculum. The wild-type microorganism was screened for production of polyurethanase on culture plates containing colloidal polyurethane and tentatively identified as *Pseudomonas chlororaphis*. This specific strain was designated as *Pseudomonas chlororaphis* BC2. The polyurethanase activity of *Pseudomonas chlororaphis* BC2, however, may be too low to permit practical production of preparations having a high polyurethanase activity.

The production of a genetically altered bacteria that produces large amounts of polyurethane starts with the collection and screening of wild-type bacteria for strains that exhibit the ability to degrade polyurethane. Appropriate wild-type bacteria may be collected, for example, by isolating bacteria strains from polyurethane-based paint fragments that have been exposed to the elements.

These isolated strains are then screened for their ability to degrade polyurethane. The ability to degrade polyurethane can be observed, for example in an appropriate culture medium that contains colloidal polyurethane, which serves as a soluble inducer for the production of polyurethanases. The original polyurethane-Docket containing culture plate is opaque. Conversion of the semi-solid culture medium to a translucent state after inoculation with bacteria and culturing evidences that the wild-type strain produces extracellular polyurethanases.

An suitable vector is then used to introduce a transposon, along with a flanking gene for resistance to a specific antibiotic, into isolates of bacterial strains producing extracellular polyurethanases. The transposon inserts into a random locus within the genome of the bacteria. Chance insertion of the transposon into an appropriate locus provides resistance to the antibiotic and may also destroy the mechanism that normally inhibits the production and/or activity of extracellular polyurethane-degrading enzyme released into the culture medium. Then, the bacterial cultures exposed to the transposon are screened for resistance to the specified antibiotic, which, if present, indicates successful transfer of the transposon DNA into the host bacteria. A Southern Blot or similar test may then confirm the random inseration of the transposon into the genome of the host bacterium.

A wild-type polyurethanase-producing bacterial culture and the mutant bacterial cultures exhibiting resistance to the specified antibiotic are then cultured in the presence of colloidal polyurethane. The cultures are then centrifuged and the supernatant isolated. This supernatant is then assayed for the level of polyurethanase activity. Mutant bacterial cultures that produce supernatants having a polyurethanase activity significantly greater than that of the supernatant produced by the wild-type polyurethanase-producing culture are the desired over-producers of polyurethanases. The supernatant is the desired polyurethanase-containing preparation.

Any vector may be used for insertion of the transposon into the wild-type polyurethanase-producing strains. For example, the transposon can be introduced into the strains by parental matings or conjugation with a donor strain of bacteria such as *E. coli* (including, but not limited to, *E. coli* S17-1 (Miller et al., *J. Bacteriol*, 170:2575–2583 (1988), incorporated herein by reference in its entirety for all purposes) and *E. coli* SM-10 (Simon et al., *Biotechnology* 1:784–791 (1983), incorporated herein by reference in its entirety for all purposes) including a plasmid with the desired transposon flanked by a gene for resistance to a specified antibiotic, direct introduction into the recipient strain of a plasmid including the transposon (flanked by a gene for resistance to a specified antibiotic) by transformation, altering the porosity of the recipient strain's cell membrane, and transduction by phage (including, but not limited to P1) that incorporates the transposon flanked by a gene that imparts resistance to a specified antibiotic).

The transposon may be any transposon which flanks a gene that imparts resistance to a first antibiotic to which the wild-type bacterial recipient will not spontaneously acquire resistance. For example, if the recipient bacteria is *P. chlororaphis*, the transposon miniTn5 flanking a gene encoding for tetracycline resistance is a suitable transposon, since *P. chlororaphis* does not spontaneously acquire tetracycline resistance. On the other hand, a transposon that flanks a gene encoding for resistance to rifampicin would not be suitable for donation to a *P. chlororaphis* recipient, since rifampicin-resistant mutants are known to spontaneously appear in *P. chlororaphis* cultures. Transposons of the type useful in the present invention are commercially available.

If a polyurethanase-producing bacterial culture can spontaneously acquire resistance to a specified second antibiotic, distinct from the first antibiotic, this ability may be useful if the transposon is introduced by conjugation with a second, donor bacteria that is sensitive to the second antibiotic and does not spontaneously acquire resistance to the second antibiotic. Before conjugation, wild-type cultures may be cultured until antibiotic resistance to the second antibiotic spontaneously appears. After wild-type polyurethanase-producing bacteria with spontaneously acquired resistance to the second antibiotic have been subjected to conjugation with a donor bacteria, the donor bacteria may be removed by adding the second antibiotic to the culture.

The culture medium selected for the growth of the wild-type and mutated bacteria is not particularly critical, provided that the culture medium supports the growth of bacterial species of interest and includes an inducer, such as colloidal polyurethane. For culture mediums used during screening for polyurethanase-producing bacteria, the destruction of the polyurethane preferably causes a readily visible change in the culture medium, such as clearing.

Any assay method that can compare the polyurethanase activity of one supernatant to the polyurethanase activity of another may be used to select the desired mutants.

The polyurethanase isolate may be directly applied to a polyurethane-coated surface as an aqueous solution, or may be trapped within a gelatinous or semi-solid matrix before application to the surface. The range over which the pH, ionic strength and temperature at which the polyurethanase isolate exhibits noticeable activity, as well as the ranges of these parameters over which the polyurethanase preparation exhibits its highest activity, may vary somewhat from strain to strain. Generally, the polyurethanase isolates will be useful at temperatures of about 10° C. to about 37° C., ionic strength of about 0% to about 30%, and pH of about 6 to about 9. The polyurethanases isolates will generally be most useful at about 20° C. to about 30° C., ionic strength of about 5% to about 20%, and pH of about 6.5 to 8.5.

Having described the invention, the following examples are given to illustrate specific applications of the invention including the best mode now known to perform the invention. These specific examples are not intended to limit the scope of the invention described in this application.

EXAMPLES

Example 1

Isolation of the Polyurethane-Degrading Bacteria

Bacterial strains and culture conditions were isolated from polyurethane-based paint fragments collected at a naval paint stripping facility. Isolated strains were screened for the production of polyurethane-degrading enzymes (hereafter referred to as polyurethanases) using semi-solid culture plates embedded with colloidal polyester polyurethane. Colloidal polyurethane culture plates were prepared by adding autoclaved polyurethane (Impranil, Mobay Corp, Pittsburgh, Pa.) to agar to a final concentration of 0.6 mg of polyurethane $ml^{-1}$ agar. The nutrient agar used for embedding the colloidal polyurethane consisted of 10 mg of yeast extract, 1 g of $K_2HPO_4$, 0.5 g of $MgSO_4$, 2 mg of $MnCl_{21}$, 0.028 of $CuCl_2$, 0.022 mg of $ZnCl_2$, 0.04 mg of $CaCl_2$, 0.14 mg of $FeCl_3$, and 10 g of agar per liter of distilled water. Colloidal polyurethane appears opaque when suspended in the semi-solid medium of a culture plate, but becomes translucent upon hydrolysis by bacterial enzymes. Strains which degrade polyurethane with extracellular polyurethanases produce clearing zones around the bacterial colonies as the enzymes are produced and degrade the polyurethane embedded in the culture plate. One strain isolated by this method was identified as *P. chlororaphis* and given the strain designation, BC2, and will hereafter referred to as the wild-type strain.

Example 2

Mutagenesis of Polyurethane-Degrading Bacteria

Bacterial strains were isolated as described in Example 1. Rifampicin-resistant mutants ($Rif^R$) of *P. chlororaphis* BC2 were isolated to select from the *E. coli* donor strain, harboring the transposable element, in biparental matings. Spontaneous $Rif^R$ mutants of all eight strains were isolated by spreading 100 μl of cells from overnight cultures in L-broth onto L-agar plates containing rifampicin (100 μg $ml^{-1}$). Culture plates were incubated (25° C., 3 d) and colonies were screened for polyurethane degradation. The *P. chlororaphis* BC2 wild-type was mutagenized in biparental matings with another bacterium, *Escherichia coli* S17-1, that harbored the plasmid, pUT miniTn5::tet (Lorenzo et al., *J. Bacteriol*, Nov. 1990, p6568–6572, incorporated herein by reference in its entirety for all purposes). The plasmid contained the transposon miniTn5 flanking a gene encoding for tetracycline resistance (tet). The plasmid with the transposon transferred from the *E. coli* strain (donor strain) to the *P. chlororaphis* BC2 (recipient strain) where the pUT vector suicided allowing the transposon to insert randomly into the genomic DNA of the *P. chlororaphis* BC2. However, there are other methods for delivering a transposon into the recipient strain including transduction by phage (P1, for instance) or by conjugation with this same plasmid vector in different donor strains (*E coli* SM10, for instance) or by conjugation with strains harboring different plasmid vectors containing other transposons. In addition, the wild-type strain may be mutated by chemical mutagens or ultraviolet irradiation.

Example 3
Isolation of Polyurethanase-Overproducing Mutants

Bacterial strains were mutagenized as described in Example 2. Exconjugants of *P. chlororaphis* BC2 were screened for extracellular polyurethanase activity. Polyurethane degradation was visualized as clearing zones around colonies of the wild-type strain *P. chlororaphis* BC2 and various transposon-generated mutants. After mating and initial screening of 10,000 exconjugants, 13 putative polyurethanase-overproducers were recultured on plates with and without colloidal polyurethane (0.6 mg ml$^{-1}$). Polyurethane degradation, visible as a clearing zone around the colony, was substantially greater for mutants *P. chlororaphis* BC2-2, -4, -5, -9, -11, and -12 than that for the wild-type, while mutants BC2-3, -8, -10, and -13 are not different from the control. Southern blot hybridization of 12 exconjugates of *P. chlororaphis* indicated that the mutagenesis method was successful in generating strains with single mutations and without obvious insertional 'hot spots' in the host genome.

Example 4
Isolation of Polyurethanase Enzyme

Bacterial strains were isolated as described in Example 3. Wild-type *P. chlororaphis* BC2 and mutants BC2-1 and BC2-12 were selected for further analysis of polyurethanase activity in batch culture. Polyurethane degradation by wild-type strain *P. chlororaphis* and polyurethanase-overproducing mutants, BC2-1 and BC2-12, was measured in batch cultures over 72 h. Both the wild-type *P. chlororaphis* and mutants were cultured in 1 liter of L-broth with the appropriate antibiotics (25° C., 72 h). Periodically, samples were removed for measurement of polyurethanase activity and protein content. Polyurethane degradation was determined by measuring the decrease in light scattering of colloidal polyurethane in Tris buffer (50 mM, pH 7.0, 1 ml). Samples from bacterial cultures were centrifuged (30 min, 10 000 x g) and 20 µl of the supernatant was added to 980 µl of a colloidal polyurethane suspension (0.1 mg Impranil ml$^{-1}$). Decrease in light scattering by the sample ($A_{600}$) was used as a measure of polyurethanase activity. Total soluble protein was determined for these samples by BCA assay (Pierce, Rockford, Ill.) using bovine serum albumin as a standard.

Supernatants of all *P. chlororaphis* strains had higher polyurethanase activity when grown in the presence of colloidal polyurethane though activity with BC2-1 and BC2-12 was greatest. However, none of the three strains of *P. chlororaphis* produced polyurethanase in the absence of the colloidal polyurethane inducer. These BC2-1 and BC2-12 mutants appear to be hypersensitive to presence of the colloidal polyurethane and either may produce increased amounts of the polyurethane-degrading enzymes, or produce conditions which enhance the activity of the enzymes.

Example 5
Application of Polyurethanase for Degradation of Polyurethane Coatings Polyurethanase was isolated as described in Example 4. Polyurethanase from *P. chlororaphis* BC2-12 is most active from 20–30° C. and at a pH range of 7.5 to 8.5. It may be applied in aqueous solution directly to the polyurethane coated surface, or may be entrapped in a gelatinous or semi-solid matrix and then applied to the surface.

Obviously, many modifications and variations of the present invention are possible in light of the above teachings. It is therefore to be understood that, within the scope of the appended claims, the invention may be practiced otherwise than as specifically described.

What is claimed is:

1. A biologically pure culture of *Pseudomonas chlororaphis* designated as ATTC No. 55729.

2. A method for the preparation of polyurethanase, comprising the steps of:

fermenting said biologically pure culture of said bacteria of claim 1 in a culture medium including an inducer for the production of polyurethanase, whereupon said bacteria produce extracellular polyurethanase; and separating said extracellular polyurethanase from said bacteria.

3. The method of claim 2, wherein said inducer is a soluble oligomer of polyurethane.

4. The method of claim 3, wherein said inducer is colloidal polyurethane.

* * * * *